United States Patent
Jang

[11] Patent Number: 6,123,087
[45] Date of Patent: Sep. 26, 2000

[54] DENTAL FLOSS HOLDER

[76] Inventor: Seung Gi Jang, 13135 Casa Linda La., #B, Garden Grove, Calif. 92844

[21] Appl. No.: 09/374,302

[22] Filed: Aug. 16, 1999

[51] Int. Cl.$^7$ .................................................. A61C 15/00
[52] U.S. Cl. ........................................... 132/325; 132/326
[58] Field of Search ................................... 132/324, 325, 132/326, 327

[56] References Cited

U.S. PATENT DOCUMENTS

| | | | |
|---|---|---|---|
| 1,260,011 | 3/1918 | Muchow | 132/324 |
| 2,052,520 | 8/1936 | Sonnenberg | 132/324 |
| 2,724,390 | 11/1955 | Sooloski | 132/326 |
| 4,574,823 | 3/1986 | Uriss | 132/325 |
| 5,052,420 | 10/1991 | Chen | 132/325 |
| 5,375,615 | 12/1994 | Wahlstrom | 132/325 |

*Primary Examiner*—Todd E. Manahan

[57] ABSTRACT

A dental floss holder, having a floss dispensing function, a floss holding function and a floss cutting function, is disclosed. In the holder, the floss holding arm, having two floss guide stems, has a structure agreeable with an oral cavity. In addition, an externally-threaded floss chamber is closed by an internally-threaded cap. A floss drum, held on a shaft in the chamber, is normally stopped by a compression force generated by both the chamber and the cap when the cap is fully tightened on the chamber. However, the floss drum is selectively released from the compression force and is rotatable around the shaft when the cap is loosened. In the floss holder, the free end of the floss is firmly fixed by an internally-threaded fixing plug movably engaging with an externally-threaded projection, thus being almost completely prevented from being unexpectedly released while drawing between the teeth. The floss holder also has a cutter used for removing a used part of the floss. The floss, drawn out of the floss chamber, is sanitarily kept by a removable cover attached to the top portion of a hand grip.

2 Claims, 3 Drawing Sheets

DENTAL FLOSS HOLDER

BACKGROUND OF THE INVENTION

1. Field of the Invention

The present invention relates, in general, to a dentalfloss holder used for dispensing and tightly holding dentalfloss and, more particularly, to a structurally improved dentalfloss holder, with a floss dispensing unit, a floss holding unit and a floss cutting unit being integrated into a single body and allowing users to more conveniently and sanitarily use the dentalfloss.

2. Description of the Prior Art

As well known to those skilled in the art, dentalfloss is a soft, strong, waxed or unwaxed thread, usually made of nylon, for drawing between the teeth to remove food particles and prevent the buildup of plaque, and is also referred to simply as "floss". In the following description, the dentalfloss will thus be referred as floss.

In the prior art, such floss is usually held by the fingers while drawing between the teeth. However, this is very inconvenient to users since the fingers, holding both ends of the floss, have to be moved in all directions within an oral cavity, having a limited space, while drawing the floss between the teeth.

In an effort to overcome the above-mentioned problem experienced in such a manual handling of the floss, several types of floss holders have been proposed and used. Some of the typical floss holders are designed to have a floss dispensing function in addition to a floss holding function.

Examples of known floss holders, having a floss dispensing function in addition to a floss holding function, may be referred to U.S. Pat. No. 4,574,823 allowed to Uriss, U.S. Pat. No. 5,052,420 allowed to Chen, and U.S. Pat. No. 5,060,681 allowed to Westbrook. However, the above U.S. floss holders are problematic in that they have a structure designed to be not agreeable with the structure of the oral cavity. In addition, a floss dispensing unit of the above floss holders uses a complicated drive means, such as a ratchet mechanism or rack and pinion gears, and so it is somewhat difficult to manufacture the floss holders. The complicated drive means for the floss dispensing unit also reduces durability of the floss holders. Another problem, experienced in the above U.S. floss holders, resides in that they individually hold the free end of the floss at a floss holding projection which has a structural defect failing to stably and firmly hold the floss. The floss holding projection thus sometimes unexpectedly releases the free end of the floss while drawing between the teeth. In the above floss holders, the floss, extending from the floss dispensing unit to a floss holding unit, is directly exposed to the outside of the holders, thereby being badly affected by atmospheric impurities, such as dust. It is thus almost impossible for the typical floss holders to hygienically keep the floss. Due to the above-mentioned problems, some people avoid using the floss even though they well know the dental beneficial effects of the floss.

SUMMARY OF THE INVENTION

Accordingly, the present invention has been made keeping in mind the above problems occurring in the prior art, and an object of the present invention is to provide a floss holder, which is designed to have a floss dispensing function, a floss holding function and a floss cutting function, which has a floss holding arm with a structure being agreeable with the structure of an oral cavity, and which allows users to more conveniently and sanitarily use the floss.

Another object of the present invention is to provide a floss holder, which has a simple screwed type structure capable of normally stopping a floss drum in a floss chamber using a compression force generated by fully tightening a nut cap on an externally-threaded opening of the floss chamber and selectively releasing the floss drum by loosening the cap so as to allow the drum to be rotatable in the chamber, and which thus simplifies the structure for controlling a rotating action of the drum in the chamber and is almost free from being broken, and is easily produced through a simple process.

A further object of the present invention is to provide a floss holder, which firmly fixes the free end of the floss by a screwed type fixing means, thus almost completely preventing the free end of the floss from being unexpectedly released while drawing between the teeth.

Still another object of the present invention is to provide a floss holder, which sanitarily keeps the floss, drawn out of the floss chamber, by covering the floss using a removable cover, the cover closing the top portion of a hand grip and protecting the floss from hands or atmospheric impurities.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
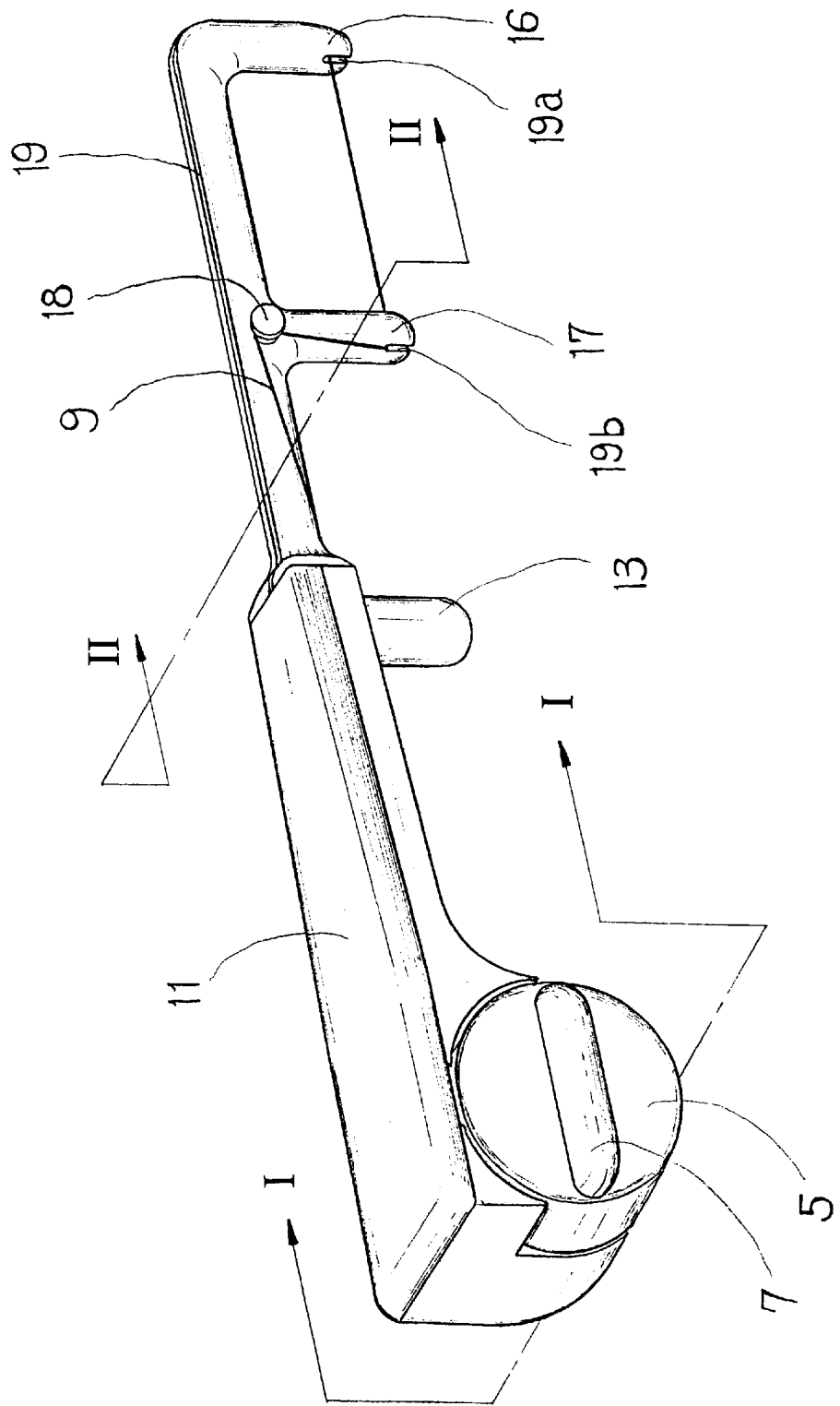
FIG. 1 is a perspective view of a floss holder in accordance with the preferred embodiment of the present invention.

As shown in FIGS. 1 to 4, the floss holder according to the preferred embodiment of this invention comprises a hand grip 1 and a floss holding arm 15 which are integrated into a single body. A cylindrical floss chamber 2, having a circular opening at one end thereof, is transversely defined in the end portion of the hand grip 1. In the above chamber 2, a floss drum holding shaft 3 integrally extends from the center of the chamber's end wall to a length. A floss drum 8 is removably set in the floss chamber 2 while being fitted over the shaft 3. An annular support rib 4 is integrally formed at the base of the above shaft 3. The above support rib 4 is designed to selectively generate a reaction force when a nut cap 5 is fully tightened on the externally-threaded circular opening of the floss chamber 2 with an annular compression rib 6 of the cap 5 generating a compression force so as to compress and stop the floss drum 8 in the chamber 2 in cooperation with the support rib 4.

That is, the floss chamber 2 has external threads at a position around the circular opening, while the cap 5 has internal threads. The opening of the chamber 2 is thus closed by the cap 5, with the internal threads of the cap 5 coming into engagement with the external threads of the floss chamber 2. The above cap 5 has two objectives. One of the two objectives is to close the circular opening of the chamber 2. The other objective of the cap 5 is to normally compress and stop the floss drum 8 in the chamber 2 and to selectively release the drum 8 so as to allow the drum 8 to be rotatable around the shaft 3 in the chamber 2. In order to accomplish the second objective, the cap 5 has the annular compression rib 6, having the same diameter as that of the annular support rib 4 of the shaft 3, at the center on its internal surface. When the cap 5 is fully tightened on the circular opening of the chamber 2, the compression rib 6 compresses and stops the floss drum 8 in the chamber 2 in cooperation with the support rib 4 of the shaft 3. However, when the cap 5 is appropriately loosened, the rib 6 releases the floss drum 8, thus allowing the drum 8 to be rotatable around the shaft 3. In order to stably and firmly stop the floss drum 8 in the chamber 2 without failure, it is necessary to design the interval between the two ribs 4 and 6, with the cap 5 being fully tightened, to be less than the width of the floss drum 8. The cap 5 also has a finger-operable knob 7 on its external surface, thus allowing a user to more conveniently and stably handle the cap 5 outside the floss holder while tightening or loosening the cap 5. The top portion of the hand grip 1 has a floss guide channel 1a, which axially extends from the chamber 2 along the grip 1 and is used for guiding floss 9 drawn out of the chamber 2 to the floss holding arm 15. The hand grip 1 is covered with a top cover 11 at the top portion. In such a case, the above cover 11 removably engages with two guide rails 10 formed along opposite sides of the top portion of the hand grip 1. Since the cover 11 is removable from the hand grip 1, the cover 11 allows a user to easily draw the free end of floss 9 out of the chamber 2 when a floss drum 8 is newly installed in the chamber 2. The cover 11 also keeps the floss 9 sanitarily.

An externally-threaded projection 12 integrally extends downwardly to a length from the floss holder at a position around the junction between the hand grip 1 and the floss holding arm 15. An internally-threaded floss fixing plug 13 movably and externally engages with the above projection 12. The objective of the fixing plug 13 is to selectively fix and hold the free end of the floss 9. That is, the free end of the floss 9 is wound around the projection 12, and is fixed on the projection 12 by fully tightening the plug 13 on said projection 12. In such a case, the floss 9 passes over floss guide slits 19a and 19b, formed at the outside ends of two floss guide stems 16 and 17 of the floss holding arm 15, and is wound around a floss winding knob 18 while being stretched prior to being fixed to the projection 12. The structure of the two guide stems 16 and 17 and the winding knob 18 will be described later herein. A cutter 14 is provided at the lower portion of the hand grip 1 at a middle position of the grip 1. The above cutter 14 is used for eliminating a used part of the floss 9 prior to drawing a new length of floss 9 between the teeth. This always allows a user to sanitarily use the floss 9.

Figure 2:
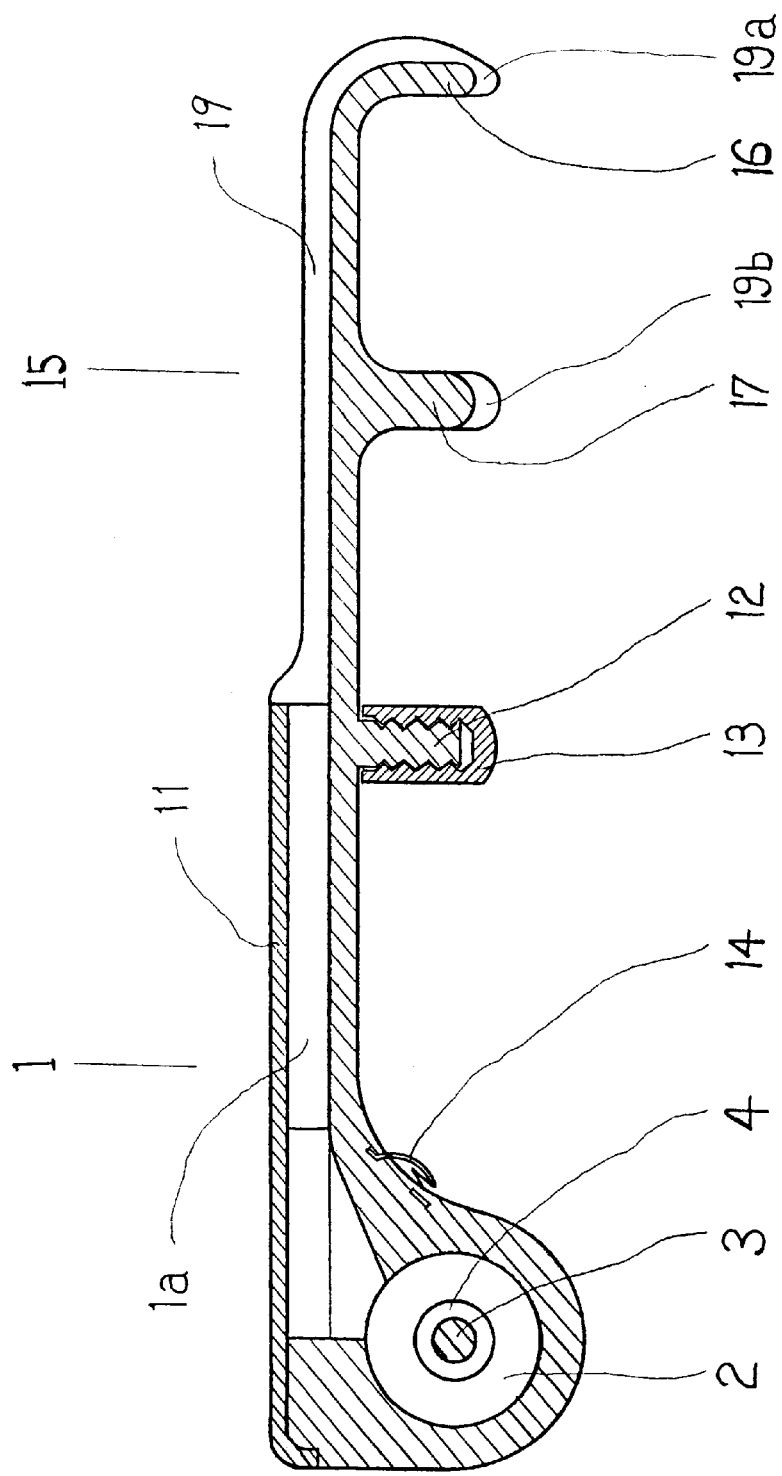
FIG. 2 is a sectional view of the floss holder of this invention.
Figure 4:
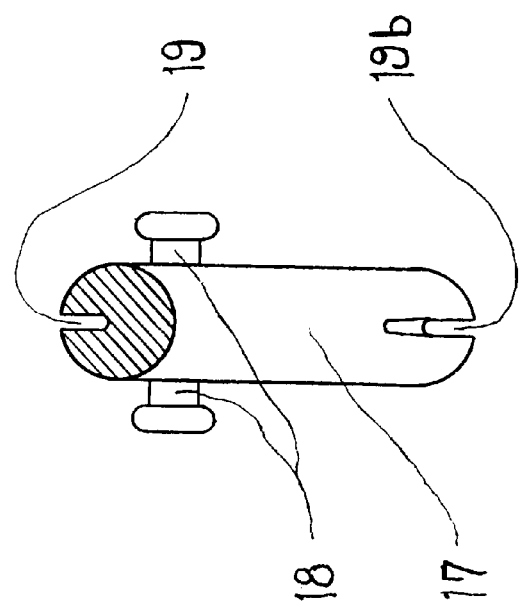
FIG. 4 is a sectional view of the above floss holder taken along the line B—B of FIG. 1.
Figure 3:
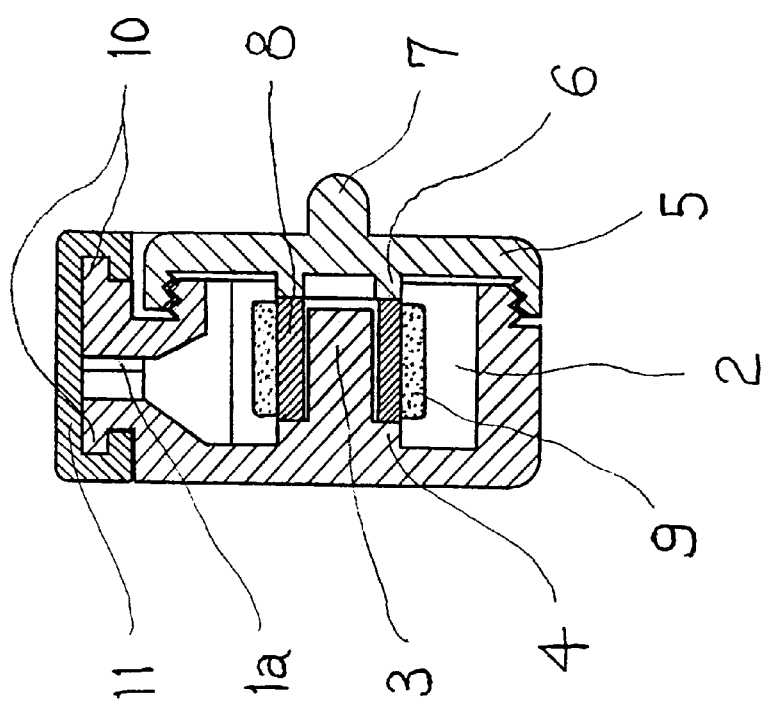
FIG. 3 is a sectional view of the above floss holder taken along the line A—A of FIG. 1.

The floss holding arm 15 integrally and axially extends from the hand grip 1 at a position opposite to the chamber 2. The above arm 15 is used for holding the floss 9, drawn out of the floss chamber 2, while stretching the floss 9 with an appropriate tension. The floss holding arm 15 has two floss guide stems, or the front guide stem 16 and a rear guide stem 17. The front guide stem 16 integrally and perpendicularly extends from the outside end of the floss holding arm 15 to a length. On the other hand, the rear guide stem 17 integrally and perpendicularly extends from a middle portion of the floss holding arm 15 in the same direction as that of the front guide stem 16. The two guide stems 16 and 17 thus form a U-shaped profile in cooperation with the spine of the floss holding arm 15. The floss holding arm 15 also has two floss winding knobs 18 at opposite sides of the base of the rear guide stem 17. A floss guide groove 19 is axially and continuously formed along the back of the floss holding arm 15. In such a case, the guide groove 19 extends from the floss guide channel 1a of the hand grip 1 while communicating with the channel 1a, and reaches the end of the front guide stem 16 as shown in FIG. 2. This drawing also shows that each floss guide stem 16, 17 has a floss guide slit 19a, 19b at its outside end. In such a case, the floss guide slit 19a of the front guide stem 16 communicates with the floss guide groove 19. The above floss guide groove 19 and the two floss guide slits 19a and 19b form a floss passage which linearly guides the floss 9 from the chamber 2 of the hand grip 1 to the rear guide stem 17 without allowing the floss 9 to be removed from its desired passage. In such a case, the floss 9 is stretched between the two floss guide stems 16 and 17 while passing over the floss guide slits 19a and 19b. In the floss holder of this invention, the externally-threaded projection 12, engaging with the internally-threaded fixing plug 13, is spaced apart from the rear guide stem 17 at an appropriate interval. This interval allows the buccinator of a user to be positioned between the plug covered projection 12 and the rear guide stem 17 when the floss holder is used for drawing between the molar teeth. That is, when it is necessary to draw the floss 9 between the molar teeth, the floss holding arm 15 is inserted into the oral cavity with the rear guide stem 17 being positioned on the interior wall of the buccinator and the plug covered projection 12 being positioned on the external cheek. In such a case, the front guide stem 16 is positioned inside the molar teeth. After positioning the floss holder relative to the oral cavity as described above, the floss holder is manually and appropriately pulled outwardly, thus biasing the buccinator in the same direction while forming a space between the rear guide stem 17 and the molar teeth in the oral cavity. Due to such a space defined between the rear guide stem 17 and the molar teeth, it is easy to draw the floss 9 between the molar teeth.

The two floss winding knobs 18, formed at opposite sides of the base of the rear guide stem 17, are either used for winding the floss 9 thereon while appropriately stretching the floss 9 after the floss 9 from the chamber 2 passes through the guide groove 19 of the floss holding arm 15 and passes over the guide slits 19a and 19b of the two floss guide stems 16 and 17. When the floss 9 is wound around either floss winding knob 18 while being stretched as described above, the floss 9 is tightly suspended between the two floss guide stems 16 and 17. Since the two floss winding knobs 18 are provided at opposite sides of the rear guide stem 17, a user, regardless of being a right- or left-handed, conveniently tensions the floss 9, suspended between the two floss guide stems 16 and 17, by winding the floss 9 on either floss winding knob 18 while stretching the floss 9.

The operational of the above floss holder will be described hereinbelow.

When it is necessary to newly install a floss drum in the chamber 2 or to change an empty floss drum with a new drum, the new drum 8 is installed as follows.

Both the cap 5 and the top cover 11 are removed from the hand grip 1 prior to fitting the new floss drum 8 over the shaft 3 in the chamber 2. The cap 5 is, thereafter, half tightened on the chamber 2 so as to allow the floss drum 8 to be held on the shaft 3 in the chamber 2 while being rotatable around the shaft 3. After installing the floss drum 8 in the chamber 2, the free end of the floss 9 of the drum 8 is drawn out of the chamber 2 using the fingers until the free end of the floss 9 reaches the floss holding arm 15. In such a case, the floss 9 passes through the channel 1a of the hand grip 1 prior to reaching the floss holding arm 15. The top portion of the hand grip 1 is, thereafter, closed by the top cover 11 which engages with the two guide rails 10 formed on the top portion of the hand grip 1. After closing the top portion of the grip 1 by the top cover 11, the floss 9 is manually pulled until the free end of the floss 9 reaches the cutter 14 after passing through the axial guide groove 19 and passing over the guide slits 19a and 19b of the two floss guide stems 16 and 17. Thereafter, the cap 5 is fully tightened on the opening of the chamber 2, thus generating a compression force by the two ribs 4 and 6 and thereby compressing and stopping the floss drum 8 in the chamber 2. The floss drum 8 is not rotatable, and so it is impossible to unwind the floss 9 from the drum 8. The floss 9 is, thereafter, stretched with an appropriate tension prior to being wound around either floss winding knob 18 at two or three turns. The floss 9 from either floss winding knob 18 is wound around the projection 12 at one or two turns before the internally-threaded fixing plug 13 is fully tightened on the externally-threaded projection 12. The free end of the floss 9 is thus finally fixed on the projection 12 by the fixing plug 13. In such a case, the floss 9 is stretched between the two floss guide stems 16 and 17 with an appropriate tension. The tensioned floss 9, stretched between the two guide stems 16 and 17 of the holder, is thus effectively used for drawing between the teeth.

After completely drawing the floss 9 between the teeth, it is necessary to eliminate the used part of the floss 9. In order to remove the used part of the floss 9, the fixing plug 13 is loosened so as to allow the floss 9 to be released from the projection 12. The floss 9 is also unwound from either floss winding knob 18 prior to newly drawing the floss 9 out of the chamber 2. In order to newly draw the floss 9 from the chamber 2 as described above, the cap 5 is appropriately loosened until the cap 5 allows the drum 8 to be rotatable around the shaft 3. The floss 9 is, thereafter, drawn out of the chamber 2 until a new portion of the floss 9, positioned around the front guide stem 16 during a previous drawing between the teeth, reaches the cutter 14. The cap 5 is, thereafter, fully tightened on the chamber 2, thus firmly stopping the drum 8 in the chamber 2. After stopping the floss drum 8, the used part of the floss 9, or the part from the free end to the portion previously positioned around the front guide stem 16, is removed by the cutter 14. The newly drawn part of the floss 9 is, thereafter, held by the floss holding arm 15 in the same manner as that described above.

The present invention provides a floss holder. This floss holder has a floss dispensing function, a floss holding function and a floss cutting function. In the floss holder, the floss holding arm has a structure designed to be agreeable with the structure of an oral cavity, thus allowing users to more conveniently use the floss. The floss holder has a simple screwed type structure capable of normally stopping a floss drum in a floss chamber using a compression force generated by fully tightening a nut cap on an externally-threaded opening of the floss chamber and selectively releasing the floss drum by loosening the cap so as to allow the drum to be rotatable in the chamber. The floss holder thus simplifies the structure for controlling a rotating action of the drum in the chamber and is almost free from being broken, and is easily produced through a simple process.

The floss holder also firmly fixes the free end of the floss by a screwed type fixing means, thus almost completely preventing the free end of the floss from being unexpectedly released while drawing between the teeth. Another advantage of the above floss holder resides in that it sanitarily keeps the floss, drawn out of the floss chamber, by covering the floss using a removable cover, which closes the top portion of a hand grip and protects the floss from hands or atmospheric impurities.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A dental floss holder, comprising:

a hand grip consisting of:
  a cylindrical floss chamber transversely defined in a first end portion of said hand grip with an opening being formed at one end of the chamber, said chamber having a floss drum holding shaft integrally extending from a center of a chamber's end wall to a length, said drum holding shaft being used for holding a floss drum thereon and having an annular support rib at a base thereof;
  a removable cap coming into screwed-type engagement with the opening of the floss chamber, said cap having a finger-operable knob on its external surface and an annular compression rib on its internal surface;
  a top cover removably engaging with two guide rails formed along opposite sides of a top portion of said hand grip, thus normally closing the top portion of the hand grip while keeping dentalfloss, drawn out of the floss chamber, sanitarily;
  an externally-threaded projection integrally extending downwardly from a lower portion of said hand grip to a length at a position around a second end portion of the hand grip, said projection movably engaging with an internally-threaded floss fixing plug so as to selectively fix and hold a free end of the dentalfloss; and
  a cutter provided at the lower portion of the hand grip at a middle portion of said grip and used for removing a used part of the dentalfloss prior to drawing a new length of dentalfloss between the teeth; and a floss holding arm integrally and axially extending from a second end portion of said hand grip and used for holding the dental floss, drawn out of the floss chamber, while stretching the dental floss with an appropriate tension, said floss holding arm consisting of:
  front and rear floss guide stems integrally and perpendicularly extending from an outside end portion and a middle portion of said floss holding arm respectively, thus forming a U-shaped profile in conjunction with a spine of the floss holding arm, said two floss guide stems individually having a floss guide slit at an outside end thereof;
  two floss winding knobs formed at opposite sides of a base of said rear floss guide stem; and
  a floss guide groove axially and continuously formed along a back of the floss holding arm and communicating with the floss guide slit of said front guide stem.

2. The dentalfloss holder according to claim 1, wherein said floss drum, held on said floss drum holding shaft, is normally compressed by both the support rib of said drum holding shaft and the compression rib of said cap with the cap being fully tightened on the floss chamber, and is selectively rotatable around the shaft with the cap being loosened.

* * * * *